United States Patent [19]

Groen

[11] 4,407,753

[45] Oct. 4, 1983

[54] 8α-OESTRA-1,3,5(10)-TRIENE DERIVATIVES, PROCESSES FOR THEIR PREPARATION AND PHARMACEUTICAL COMPOSITIONS

[75] Inventor: Marinus B. Groen, Schayk, Netherlands

[73] Assignee: Akzo N.V., Arnhem, Netherlands

[21] Appl. No.: 280,266

[22] Filed: Jul. 2, 1981

[30] Foreign Application Priority Data

Jul. 11, 1980 [NL] Netherlands ......................... 8003999

[51] Int. Cl.³ .............................................. C07J 71/00
[52] U.S. Cl. ........................ 260/239.55 R; 260/397.45
[58] Field of Search ........................... 260/397.5, 239.55

[56] References Cited

U.S. PATENT DOCUMENTS 3,951,959 4/1976 Prezewowsky et al. ......... 260/397.5
3,983,144 9/1976 Leemhuis .......................... 260/397.5
4,066,674 1/1978 Eder et al. ......................... 260/397.5

Primary Examiner—Elbert L. Roberts
Attorney, Agent, or Firm—Abelman, Frayne & Rezac

[57] ABSTRACT

The invention relates to new 8α-oestra-1,3,5(10)-triene derivatives having the formula:

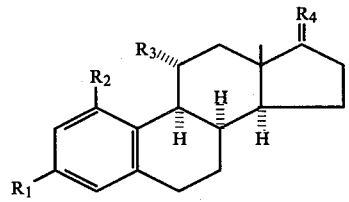

in which
  $R_1$=H or a free, esterified or etherified hydroxy group;
  $R_2$=H or a free, esterified or etherified hydroxy group, with the proviso that at least one of the substituents $R_1$ and $R_2$ is different from H;
  $R_3$=alkyl (1–4 C) and
  $R_4$=O or ($\alpha$X) ($\beta$Y), in which
    X=H or aliphatic hydrocarbyl (1–4 C) and
    Y=a free, esterified or etherified hydroxy group and the enantiomers and racemic mixtures thereof, and also extends to processes for their preparation and to pharmaceutical compositions containing said new compounds.

1 Claim, No Drawings

8α-OESTRA-1,3,5(10)-TRIENE DERIVATIVES, PROCESSES FOR THEIR PREPARATION AND PHARMACEUTICAL COMPOSITIONS

The invention relates to new 8α-oestra-1,3,5(10)-triene derivatives, processes for preparing these new 8α-steroids and to pharmaceutical compositions containing one or more of these new 8α-steroids as active constituent. The invention relates particularly to new 8α-oestra-1,3,5(10)-triene compounds having an 11α-alkyl(1-4 C) substituent.

8α-steroids (or 8-iso-steroids) of the oestrane series are already known, see for example, J.A.C.S. 80, 661 (1958); J.Med.Chem. 9, 338 (1966), Steroids 28, 325 (1976), U.S. Pat. No. 3,465,011.

A group of new 8α-oestra-1,3,5(10)-triene derivatives with interesting biological properties has now been discovered, which is substituted at the 11α-position by an alkyl group having 1-4 carbon atoms. The new 8α-compounds have the following formula (1):

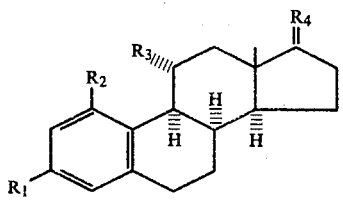

wherein $R_1$ = H or a free, esterified or etherified hydroxy group $R_2$ = H or a free, esterified or etherified hydroxy group, with the proviso that at least one of the substituents $R_1$ and $R_2$ is dissimilar to H $R_3$ = alkyl (1-4 C); and $R_4$ = O or (αX) (βY), in which X = H or aliphatic hydrocarbyl (1-4 C) and Y = a free, esterified or etherified hydroxy group.

The group of new 8α compounds comprises not only the compounds with the natural configuration indicated above by the formula, but also the enantiomers thereof, and racemic mixtures.

The new 11α-alkyl-8α-oestra-1,3,5(10)-trienes with formula I are valuable because of their oestrogenic, anti-oestrogenic, uterotropic and ovulation-inhibiting properties. The new compounds exhibit especially an interesting dissociation between uterotropic and vaginotropic effect as compared with the 8α-compounds without 11α-alkyl-substituent.

The following can also be stated as regards the substituents $R_1$–$R_4$:

$R_1$ is preferably a hydroxy group, which may be esterified or etherified or not, for example hydroxy, hydrocarbyloxy (1-8 C), such as methoxy, ethoxy, cyclopentoxy, cyclohexenyloxy or benzyloxy; trimethylsilyloxy; tetrahydropyranyloxy or carboxyacyloxy (1-7 C), such as acetoxy, propionoxy, pivaloyloxy or benzoyloxy. The highest preference for $R_1$ is given to hydroxy, methoxy or acetoxy.

$R_2$ is preferably H or identical with $R_1$.

$R_3$ is preferably methyl or ethyl.

$R_4$ is preferably (αX) (βOH) or (αX) (βOacetyl).

The aliphatic hydrocarbyl group possibly present in $R_4$ and having 1-4 carbon atoms is a saturated or unsaturated hydrocarbon residue, e.g. methyl, ethyl, propyl, butyl, isopropyl, vinyl, propenyl, allyl, ethynyl, propynyl, propargyl, butynyl, propadienyl, or butadienyl. A preferred group is ethynyl.

The new compounds can for example be prepared starting with the corresponding 11-oxo compound. 11-oxo-8α-oestradiol derivatives are for example already known from the American Pat. No. 3,465,011.

The 11-oxo-8α-compound is Grignarded with an alkyl-Q-compound, in which Q is Li or a magnesium halide residue, e.g. MgBr or MgI. The 11-alkyl-11-hydroxy compound thus obtained is dehydrated, e.g. using thionyl-chloride/pyridine, to the corresponding 11-alkyl-$\Delta^{9(11)}$-compound, from which the desired 11β-alkyl-8α-compound is obtained by reduction of the double bond between $C_9$ and $C_{11}$, e.g. by means of an alkali metal in liquid ammonia, such as Li/NH$_3$ or Na/NH$_3$.

Another extremely suitable method of preparation is a biomimetic total synthesis in accordance with a modified Johnson synthesis, where a suitable (Z)-olefinic polyene is stereo-selectively cyclized to a 11α,17-dialkyl-8α-gona-1,3,5(10),13(17)-tetraene. Epoxidization of the 13(17)-olefine obtained and opening up of the epoxide ring under weakly acid conditions gives rise to a migration of the 17-alkyl group to position 13, whereby the corresponding 13β-alkyl-17-ketone forms.

The biomimetic total synthesis takes place in accordance with scheme A (see page 5), in which $R_1$, $R_2$, $R_3$ and $R_4$ have the meanings already allocated A = O or P($R_9$)$_3$, in which $R_9$ = an aryl hydrocarbon group with 6 or 7 carbon atoms, preferably phenyl;

Z = O or P($R_9$)$_3$, in which $R_9$ has the significance already allocated, on the understanding that Z = O, when A = P($R_9$)$_3$ and conversely, whereby preferably A = P($R_9$)$_3$ and Z = O;

$R_7$ = H or CH$_3$, and $R_8$ = H or CH$_3$, on the understanding that $R_8$ = H if $R_7$ = CH$_3$ and $R_8$ = CH$_3$ if $R_7$ = H.

$R_5$ and/or $R_6$ = hydroxy, hydrocarboxyloxy (1-8 C), such as methoxy, ethoxy, cyclopentoxy, cyclohexenyloxy or benzyloxy; trimethylsilyloxy; tetrahydropyranyloxy; or carboxyacyloxy (1-7 C), such as acetoxy, propionoxy, pivaloyloxy or benzoyloxy. $R_5$ and/or $R_6$ is preferably methoxy.

Reaction stage (a) is a Wittig reaction between an ylide (a phosphorane) and an aldehyde. During this reaction mainly the desired (Z) isomer (4) forms together with a small quantity (less than 10%) of the (E) isomer.

Reaction stage (b) takes place in a boiling acetic acid solution in the presence of a trace of sulphuric acid.

Reaction stage (c): The diketone (5) is cyclized with dilute base to give the cyclopentenone (6). In this stage the (E) isomer still present can best be removed, say by chromatography over silica gel. The (E) isomer is somewhat more polar than the (Z) isomer.

Scheme A:

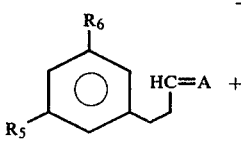

(2)

-continued
Scheme A:

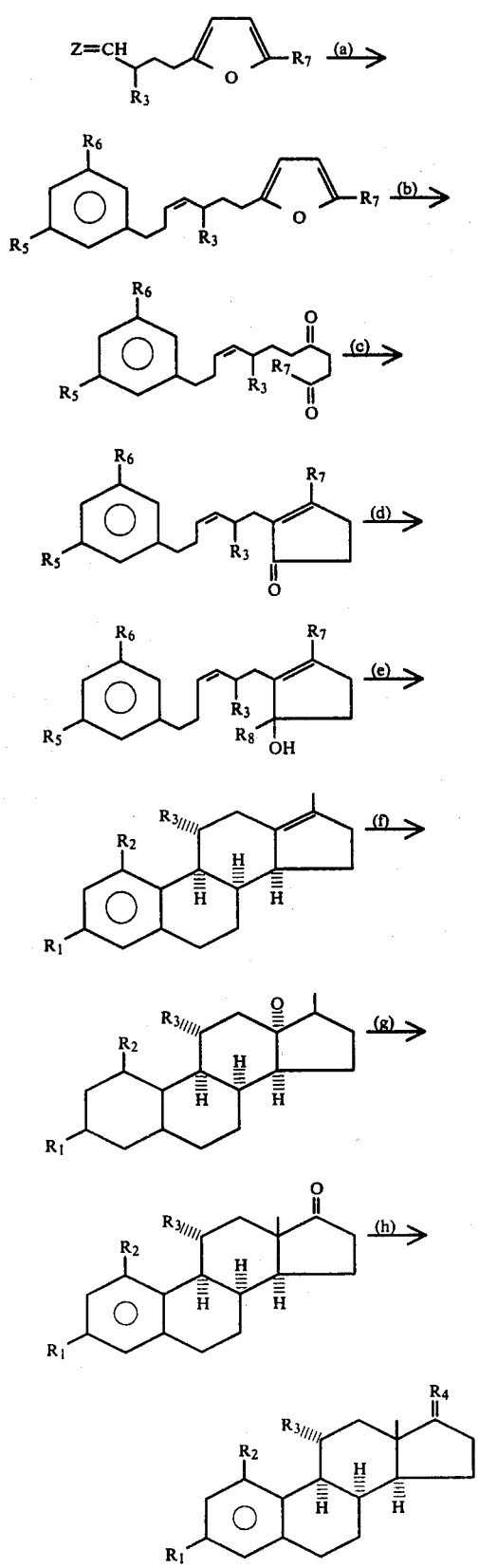

It is not necessary to attempt complete removal, because small quantities of (E) isomer (less than 5%) do not deleteriously affect the subsequent progress of the synthesis.

Reaction stage (d) comprisis a reduction of the cyclopentenone (6) to the corresponding cyclopentenol (7) in the case where $R_7=CH_3$ (and hence $R_8=H$).

The reduction of the cyclopentenone to the cyclopentenol is performed using a complex metal hydride such as lithium aluminium hydride, di-isobutyl-aluminiumhydride, sodium-di-isobutylboronhydride, at a temperature between $-25°$ C. and $0°$ C.

If $R_7=H$ then reaction stage (d) consists of Grignarding of the cyclopentenone (6) with methyl lithium or a methyl-magnesiumhalogenide which supplies the cyclopentenol (7), in which $R_7=H$ and $R_8=CH_3$.

The cyclization substrate (7) is cyclized (reaction stage (e)) under acid conditions with the aid of a Lewis acid to give a 11α-alkyl-8αH-steroid (8).

During cyclization a protic or aprotic Lewis acid is employed and the reaction is carried out in a solvent which is preferably non-nucleophilic. Examples of suitable solvents are formic acid, acetic acid, trifluoro acetic acid, trifluorethanol, nitroethane, benzene, saturated hydrocarbons such as pentane, hexane, cyclohexane and halogenated hydrocarbons such as dichloromethane.

Examples of protic Lewis acids are carbonic acids with a pK ($20°$ C.) $<4$, preferably $<2$, such as for example formic acid, trifluoro-acetic acid, trichloro acetic acid. Examples of aprotic Lewis acids are zinc chloride, zinc bromide, boron trifluoride. Preferably use is made of formic acid or zinc chloride, the amount being roughly 0.1 to 10 mol per mol cyclization substrate, preferably 0.5 to 5 mol per mol.

The cyclization reaction is normally carried out below room temperature ($20°-21°$ C.) and above $-150°$ C., preferably at a temperature between $+10°$ C. and $-100°$ C.

If in the starting product for cyclization $R_5 \neq R_6$ (e.g. $R_5$=methoxy and $R_6=H$ or conversely), then during cyclization two position-isomers can form. The ratio thereof can be influenced by the reaction conditions and by the choice of the substituents $R_5$ and $R_6$. If for example $R_5$=methoxy and $R_6=H$, then a "para-"product ($R_1$=methoxy, $R_2=H$) and an "ortho" product ($R_1=H$, $R_2$=methoxy) can form. Normally more "para" product forms than "ortho" product. In this manner we thus obtain a steroid which is substituted at the 3-position, in addition to a steroid substituted at the 1-position. Separation of these two products can be undertaken in the normal way, e.g. by chromatography. The separate products can be further purified by crystallisation, e.g. from methanol. If $R_5=R_6$, then during cyclization only one product forms, a 1,3-di-substituted steroid.

In reaction stage (f) the 13,17 double bond is epoxidized in the cyclization product (8). Epoxidation with a peroxy acid in this case supplies mainly the desired α-epoxide (9). A suitable peroxy acid is for example m-chloroperbenzoic acid. The β-epoxide formed during epoxidation, usually less than 10%, can be separated from the α-epoxide by column chromatography over deactivated alumina.

The 11α-alkyl-8α-gona-1,3,5(10),13(17)-tetraenes (8) obtained during cyclization, and the 13α,17α-epoxy derivatives obtained therefrom are also new compounds with biological activity and are at the same time important intermediate products for the preparation of the new biologically active 11α-alkyl-8α-steroids (1).

During reaction stage (g) the α-epoxide (9), by treatment with an acid, preferably aprotic Lewis acid such as borontrifluoride-etherate, in a suitable solvent for example toluene, at a temperature between −100° C. and 80° C., preferably between −40° C. and 20° C., is converted into the 8α-oestrone derivative (10).

The 8α-oestrone derivative (10) obtained in this manner appertains to the group of new 11α-alkyl-8α-oestra-1,3,5(10)-trienes of the present invention.

In this 8α-oestrone derivative (10) it is possible in a known manner to introduce other substituents at position 17 (reaction stage h). If required the substituents in the A-ring ($R_1$ and $R_2$) can also be modified by splitting off (hydrolysis) of ester or ether groups and/or esterification or etherification of hydroxy groups.

A 17-oxo group can if required be reduced to a 17β-hydroxy group, e.g. with a complex metal hydride such as lithium aluminium hydride.

The introduction of a saturated or unsaturated hydrocarbon group at position 17 is undertaken by reacting the 17-oxo steroid with a metal derivative of a saturated or unsaturated aliphatic hydrocarbon, possibly followed by a reduction of the side chains thus introduced. The metal derivative can be a Grignard compound, e.g. the magnesium bromide of the appropriate hydrocarbon, or an alkyl lithium compound.

A particular embodiment of the condensation reaction for the preparation of the 17β-hydroxy-17α-alkynyl compounds consists in reacting the 17-oxo steroid with a triply unsaturated hydrocarbon, e.g. acetylene, in the presence of an alkali metal or an alkali metal compound, such as an alkali metal amide or alcoholate, or with a metal compound of a triply unsaturated hydrocarbon such as an alkali metal or earth alkali metal compound, e.g. potassium acetylide.

The ester group possibly present in the end products at positions 1, 3 and/or 17 can be derived from a saturated or unsaturated organic carboxylic acid with 1–18 carbon atoms. The conversion of a hydroxy group into an ester group can take place in accordance with a known method, e.g. by reacting the hydroxy steroid with the appropriate acid or a functional derivative thereof, such as the anhydride or the halogenide. The esterification of the 17β-hydroxy group, which is formed during the 17-alkylation, can also take place by allowing the reaction product of the condensation of the 17-oxo steroid with a metal derivative of an unsaturated hydrocarbon residue, to react without prior hydrolysis with the corresponding acid or a functional derivative thereof. Esterification can for example also take place by allowing the steroid to react with a carboxylic acid anhydride such as acetic acid anhydride in the presence of 4-dimethyl aminopyridine, preferably at the same time in the presence of a tertiary amine such as trimethyl amine.

As examples of organic carboxylic acids which can be employed for esterification the following are mentioned: formic acid, acetic acid, propionic acid, butyric acid, valeric acid, caprinic acid, undecylic acid, lauric acid, tridecylic acid, myristic acid, pentadecylic acid, oleic acid, palmitic acid, stearic acid, adamantane carboxylic acid, trimethyl acetic acid, diethyl acetic acid, cyclohexylpropionic acid, undecylenic acid, benzoic acid, phenyl acetic acid, phenyl propionic acid, phenyl butyric acid, fumaric acid, malonic acid, succinic acid, glutaric acid, pimelic acid, and tartaric acid. As already stated it is also possible to use functional derivatives thereof such as the anhydrides or acid chlorides.

The ether groups present in the end products at positions 1, 3 and/or 17 can be derived from an aliphatic, aromatic, araliphatic or heterocyclic hydrocarbon. Examples of such ether groups are the methyl ether, ethyl ether, butyl ether, cyclopentyl ether, tetrahydropyranyl ether, cyclohexyl ether and 1'-ethoxyethyl ether group.

Etherification can take place in accordance with standard methods. The cyclopentenol (7) to be cyclized contains two chiral centres, namely the carbon atom which bears the substituent $R_8$ and the carbon atom which bears the substituent $R_3$. The stereo-chemistry of the cyclization product appears now to be governed mainly by the latter-mentioned centre. If we take as a basis a racemic mixture, then a racemic tetracyclic product appears to form consisting of 2 enantiomers, whilst because of the two chiral centres without optical induction, four stereo isomers in equal quantities should have formed. That the chiral centre in the cyclopentanol group hardly has any influence on the stereo chemistry of the cyclization product is indicated by the fact that the (S)-OH-(R)-$R_3$-substituted starting product gives the same 11α-$R_3$-substituted cyclization product as the (R)-OH-(R)-$R_3$-substituted starting product.

If an optically active starting product is taken as a basis, e.g. the (R)-$R_3$ cyclopentenol, then an optically active cyclization product (9) is formed, e.g. a natural 11α-8α-gona-1,3,5,13(17)-tetraene.

Racemic mixtures of intermediates or end products can be separated in the normal way into the optical antipodes, e.g. by reaction of the dl-steroid or a derivative thereof with an optically active acid or base, fractional crystallization or chromatography of the reaction product to obtain optically pure compounds and hydrolysis to give the pure d- and/or l-steroid.

The new compounds according to the invention may be used in the form of pharmaceutical compositions, for which purpose an effective amount thereof is mixed with one or more pharmaceutically acceptable non-toxic carriers and/or the usual excipients suitable for enteral or parenteral administration.

The invention will now be explained with the aid of the following examples.

EXAMPLE 1

(a) dl-2-Methyl-4-(5-methyl-2-furyl)-butane nitrile

A solution of 2-(3-bromobutyl)-5-methyl-furan (20.5 g) and 13 g KCN in 100 ml of dry dimethyl sulphoxide was heated during stirring for 16 hours at 50°–55° C. The mixture was cooled, diluted with water and extracted using ether. The extracts were washed with water, dried on anhydrous MgSO$_4$ and boiled down under vacuum. The residue was subjected to chromatographic adsorption over silicagel with hexane/ethyl acetate (9:1) and gave 14.6 g dl-2-methyl-4-(5-methyl-2-furyl)-butane nitrile.

This product can also be prepared starting from 4-(5-methyl-2-furyl)-butane nitrile by alkylation with methyl iodide in the presence of lithium diethyl amide in a manner similar to that described in example Va.

(b) dl-2-Methyl-4-(5-methyl-2-furyl)-butanal (formula (3): $R_3 = R_7$ = methyl, $Z = O$)

42 ml of 1,2 M di-isobutyl aluminium hydride solution in toluene was added dropwise to a solution of 8.15 g (0.05 mol) 2-methyl-4-(5-methyl-2-furyl)-butane nitrile in 250 ml dry toluene, which had been cooled down to −78° C., during stirring and under nitrogen. The solution obtained was stirred for 30 minutes at −70° C. and then poured into excess 2 N hydrochloric acid. The organic layer was separated and then washed successively with 2 N hydrochloric acid, water and sodium bicarbonate solution. The resultant solution was dried on anhydrous sodium sulphate and concentrated under reduced pressure. In this way 5.4 g (65% yield) of the desired butanal (content >90%) was obtained which without further purification was used in the Wittig reaction from example I(c).

(c)

dl-(Z)-1-(3-methoxyphenyl)-5-methyl-7-(5-methyl-2-furyl)-3-heptene (formula (4), $R_3=R_7=CH_3$, $R_5=$methoxy, $R_6=H$)

A suspension of 49.1 g (0.10 mol) 3-(3-methoxyphenyl)propyl-triphenyl phosphonium bromide in 200 ml dry tetrahydrofurane was treated under nitrogen at 0°–5° C. with 62 ml 1.62 M (0.10 ml) n-butyl lithium solution in hexane. The red solution obtained was stirred for 15 minutes, after which 15.0 g (90 mmol) dl-2-methyl-4-(5-methyl-2-furyl)-butanal dissolved in 50 ml dry tetrahydrofurane was added dropwise during stirring at 0°–5° C. The reaction mixture was mixed with water and extracted using ether (3x). The extracts were washed with water, dried on anhydrous sodium sulphate and concentrated under reduced pressure. The residue was subjected to chromatography above 200 g silicagel with hexane/ethyl acetate 9:1. This gave 19.6 g (73% yield) product with a content of 93% of the desired (Z)-isomer.

(d)

dl-2-[(Z)-6-(3-methoxyphenyl)-2-methyl-3-hexenyl]-3-methyl-2-cyclopentonone (formula (6), $R_3=R_7=CH_3$, $R_5=$methoxy, $R_6=H$)

The Wittig product from example I(c) (14.9 g, 50 mmol) was mixed with 660 ml acetic acid, 330 ml water and 15 ml of 4 N sulphuric acid. The mixture was boiled for 3 hours subject to reflux cooling, and then cooled down and mixed with 1 liter water. The mixture obtained was extracted using 4 portions of 150 ml dichloromethane. The extracts were merged, washed with water (3x) and sodium bicarbonate solution, and dried on anhydrous potassium carbonate. The solvent was evaporated under reduced pressure and the residue was put into 400 ml ethanol. A solution of 3.3 g KOH in 200 ml water was added and the mixture obtained was boiled for 4 hours under reflux cooling. The reaction mixture was cooled and, under reduced pressure, was concentrated to roughly one third of the original volume. Extraction was then undertaken using 3 portions of ethyl acetate, which was subsequently washed with water and dried on anhydrous sodium sulphate. The solvent was evaporated off and the residue obtained was subjected to chromatography above 300 g silicagel with hexane/ethyl acetate 8:2. Initially 11.0 g (74% yield) of substance was isolated having a content of roughly 95% of the desired product. Further elution gave a further 1.2 g (8% yield) of product contaminated with (E) isomer.

(e) dl-1- and dl-3-methoxy-11α,17-dimethyl-8α-gona-1,3,5(10),13(17)-tetraene (formula (8), $R_3=CH_3$, $R_1=H$, $R_2=$methoxy or $R_1=$methoxy, $R_2=H$)

At −20° C. 0.38 g (10 mmol) of lithium aluminium anhydride was added slowly to a solution of cyclopentenone from example I(d) (3.0 g, 10 mmol) in 100 ml of dry ether. The mixture was heated during stirring for about 30 minutes to 0° C., after which saturated sodium sulphate solution was carefully added dropwise. The ether laywer was decanted off from the resultant deposit, which was subsequently extracted twice again using dry ether. The merged ether layers were concentrated. The residue (cyclopentenol (7), in which $R_3=R_7=CH_3$, $R_5=$methoxy, $R_6=H$, $R_8=H$) was dissolved in 50 ml nitro ethane and, during stirring, was added dropwise to a mixture of 5.45 g (40 mmol) zinc chloride and 200 ml nitro ethane which had been cooled down to −35° C. After a further 10 minutes stirring at −35° C. the reaction mixture was poured into water and extracted with ether. The extracts were washed with water, dried on anhydrous sodium sulphate, and concentrated under reduced pressure. The residue was subjected to chromatography above 90 g silicagel with hexane/toluene 8:2. Initially the 1-methoxy isomer was eluated (0.874 g, 31% yield), followed by the 3-methoxy isomer (1.52 g, 54% yield). Recrystallisation from methanol gave 0.79 g (28% yield) of pure 1-methoxy isomer, melting point 77.5°–78° C., and 1.27 g (45% yield) pure 3-methoxy isomer, melting point 74°–75° C.

EXAMPLE II (a)

dl-3-methoxy-11α,17-dimethyl-13α,17α-epoxy-8α-gona-1,3,5(10)-triene (formule (9), $R_1=$methoxy, $R_2=H$, $R_3=$methyl)

A solution of 1.41 g (5 mmol) of the 3-methoxy isomer from example I was dissolved in 80 ml dichloromethane. The solution was cooled down to −30° C. and a solution of 1.48 g m-chloroperbenzoic acid (content 70%, 1.2 equiv.) in 20 ml dichloromethane was added slowly dropwise. The reaction mixture obtained was stirred for 15 minutes at −20° C. to −10° C. and then washed with potassium carbonate solution, dried on anhydrous potassium carbonate and concentrated. The residue was recrystallised from hexane. This gave 1.12 g (75% yield) of the desired epoxide, melting point 148°–151° C.

(b) dl-11α-methyl-8α-oestrone methyl ether (formula (10), $R_1=$methoxy, $R_2=H$, $R_3=$methyl)

A solution of 0.894 g (3 mmol) of the epoxide from example II(a) in 70 ml toluene was cooled under nitrogen to −40° C. Then during stirring 2 ml of borotrifluoride-ethanol was added and the red solution obtained was heated for about 30 minutes to −10° C. The reaction mixture was shaken with an aqueous potassium carbonate solution until colourless. The organic layer was separated out, dried on anhydrous potassium carbonate and boiled down. The residue was subjected to chromatography above 50 g silicagel with hexane/ethyl acetate 95:5–90:10. 0.322 g (36% yield) dl-11α-methyl-8α-oestrone methyl ether was isolated, melting point 136°–137.5° C. (from ether/hexane).

EXAMPLE III dl-11α-Methyl-8α-oestradiol 3-methyl ether (formula (1): $R_1$=methoxy, $R_2$=H, $R_3$=methyl, $R_4$=H(βOH))

0.10 g (2.6 mmol) of lithium aluminium hydride was added to a solution of 0.45 g (1.5 mmol) of the 8α-oestrone derivative from example II in 20 ml toluene/ether 1:1.

The mixture was stirred for 30 minutes at room temperature and subsequently processed in the manner described in example I(e). The crude product was subjected to chromatography above 15 g silicagel with hexane/ethyl acetate 8:2 and recrystallised from ether. In this way 0.36 g (80% yield) dl-11α-methyl-8α-oestradiol 3-methyl ether was obtained, melting point 129°–130.5° C.

EXAMPLE IV dl-11α-Methyl-8α-oestradiol (formula (1): $R_1$=OH, $R_2$=H, $R_3$=methyl, $R_4$=H(βOH))

A mixture of 0.36 g (1.2 mmol) dl-11α-methyl-8α-oestradiol 3-methyl ether and 2.5 g pyridine hydrochloride was heated for 1 hour to 200° C. After cooling the reaction mixture was mixed with water and extracted with 3 portions of ethyl acetate. The extracts were washed with water, dried in anhydrous sodium sulphate and concentrated. The residue was filtered over silicagel with ethyl acetate. Concentration and recrystallisation from ether gave 0.285 g (83% yield) dl-11α-methyl-8α-oestradiol, melting point 219°–221° C.

EXAMPLE V (a) dl-2-Ethyl-4-(5-methyl-2-furyl)-butane nitrile

A solution of lithium diethyl amide prepared from 0.7 g (0.1 mol) lithium and 7.3 g (0.1 mol) diethyl amine in 44 ml benzene/hexamethyl phosphoric acid triamide 1:1 (2 hours at 25° C.) was added dropwise under nitrogen to a mixture which had been cooled down to −70° C. of 14.9 g (0.1 mol) 4-(5-methyl-2-furyl)-butane nitrile, 15.6 g (0.1 mol) ethyl iodide, 20 ml dry tetrahydrofurane and 140 ml dry ether. The mixture obtained was stirred for one hour at −70° C., was slowly heated up to 10° C. and then poured into cold water. The organic layer was separated off, washed with water and dried on anhydrous magnesium sulphate. The solvent was evaporated off under reduced pressure and the residue was subjected to chromatography over 300 g silicagel with hexane/ethyl acetate 95:5. Initially 2.3 g dl-2,2-diethyl-4-(5-methyl-2-furyl)-butane nitrile was eluated, followed by 9.5 g (58% yield) dl-2-ethyl-4-(5-methyl-2-furyl)-butane nitrile.

(b) dl-2-Ethyl-4-(5-methyl-2-furyl)-butanal (formula (3): $R_3$=ethyl, $R_7$=methyl, Z=O)

The product from example V(a) was reduced in a manner analogous to that described in example I(b) to the corresponding aldehyde, with 49% yield.

(c)
dl-2-[(Z)-6-(3-methoxyphenyl)-2-ethyl-hexenyl]-3-methyl-2-cyclopentenone (formula (6), $R_3$=$C_2H_5$, $R_7$=$CH_3$, $R_5$=methoxy, $R_6$=H)

The product from example I(b) was subjected to a Wittig reaction as described in example I(c) and then converted to the cyclopentenone derivative mentioned in the preamble, in a manner similar to that described in example I(d). These reactions gave an overall yield of 62%.

(d) dl-1- and dl-3-methoxy-11α-ethyl-17-methyl-8α-gona-1,3,5(10),13(17)-tetraene (formula (8), $R_3$=$C_2H_5$, 1,3,5(10),13(17)-tetraene (formula (8), $R_3$=$C_2H_5$, $R_1$=H, $R_2$=methoxy or $R_1$=methoxy, $R_2$=H)

The cyclopentenone from example V(d) was reduced and cyclized in a manner analogous to that described in example I(e). The 1-methoxy isomer was isolated, with 12% yield, melting point 107°–108° C. (recrystallisation from methanol) and the 3-methoxy isomer with 43.6% yield, melting point 80°–90° C. (from methanol).

EXAMPLE VI dl-11α-Ethyl-8α-oestrone methyl ether (formula (10), $R_1$=methoxy, $R_2$=H, $R_3$=$C_2H_5$)

The 3-methoxy isomer from example V(d) was oxidised and reacted in a manner analogous to that described in example II. In this way dl-11α-ethyl-8α-oestrone methyl ether was obtained with 25% yield (oil).

EXAMPLE VII dl-11α-Ethyl-8α-oestradiol (formula (1): $R_1$=OH, $R_2$=H, $R_3$=ethyl, $R_4$=H(βOH))

The oestrone derivative from example VI was reduced and demethylated in the manner as described in examples III and IV. This gave dl-11α-ethyl-8α-oestradiol with 17% yield, melting point 110°–114° C.

EXAMPLE VIII dl-11α-Ethyl-17-methyl-8α-oestra-1,3,5(10),13(17)-tetraene-1-ol (formula (1): $R_1$=H, $R_2$=OH, $R_3$=ethyl, $R_4$=H(βOH))

A mixture of 2.0 g (7.6 mmol) triphenyl phosphine, 1.06 g (0.152 mol) lithium and 100 ml dry tetrahydrofuran was stirred under nitrogen at room temperature until the lithium had dissolved (about 2 hours). Then 3.0 g (10 mmol) of 1-methoxy-isomer from example V(d) and 7.5 ml tetramethyl ethylene diamine was added. The mixture obtained was boiled for 5 hours under reflux cooling, after which water was added and extracted with ethyl acetate. The extracts were washed with saturated common salt solution, dried on anhydrous sodium sulphate and concentrated. The residue was subjected to chromatography over 100 g silicagel with hexane/ethyl acetate 95:5. 3.0 g Of the product mentioned in the preamble was obtained. Recrystallisation from hexane gave a pure specimen with a melting point of 140°–142° C.

EXAMPLE IX dl-11α-Ethyl-1-hydroxy-8α-oestra-1,3,5(10)-triene-17-one benzoate (formula (1): $R_1$=H, $R_2$=benzoyloxy, $R_3$=ethyl, $R_4$=O)

The product from example VIII (3.0 g) was dissolved in 100 ml dry pyridine and treated at 0° C. with 7.0 g (5 equiv.) benzoyl chloride. After 2 hours at 0° C. the reaction mixture was poured into water and extracted with ether. The extracts were washed successively with 2 N hydrochloric acid, water and saturated sodium bicarbonate solution and dried on anhydrous sodium sulphate. The product obtained after concentration was epoxidised in the same way as described in example II(a) and then treated with borotrifluoride etherate and processed as described in example II(b). This gave 665 mg (16% yield) of pure 17-ketone-1-benzoate.

EXAMPLE X dl-11α-Ethyl-8α-oestra-1,3,5(10)-triene-1,17β-diol

The 17-ketone-1-benzoate from example IX was treated with lithium aluminium anhydride in a similar manner to that described in example III. The pure 1,17β-diol, after crystallisation from chloroform/hexane, was obtained with 68% yield, melting point 155°–157° C.

EXAMPLE XI dl-1-Hydroxy-11α-methyl-8α-oestra-1,3,5(10)-triene-17-one benzoate (formula (1), $R_1$=H, $R_2$=benzoyloxy, $R_3$=methyl, $R_4$=O)

The 1-methoxy isomer from example I(e) was reacted in a manner analogous to that described in examples VIII and IX to the benzoate mentioned in the preamble, giving 18% overall yield, melting point 138°–139° C.

EXAMPLE XII dl-11α-Methyl-8α-oestra-1,3,5(10)-triene-1,17β-diol (formula (1), $R_1$=H, $R_2$=OH, $R_3$=methyl, $R_4$=H(βOH))

The 17-ketone-1-benzoate from example XI was treated with lithium aluminium hydride in a manner analogous to that described in example III. After crystallisation from ether the pure diol was obtained with 72% yield, melting point 212°–213° C.

EXAMPLE XIII dl-3-Hydroxy-11α-methyl-8α-oestra-1,3,5(10)-triene-17-one-benzoate (formula (1), $R_1$=benzoyloxy, $R_2$=H, $R_3$=methyl, $R_4$=O)

The 3-methoxy-isomer from example I(e) was reacted in a manner analogous to that described in examples VIII and IX to the 17-ketone-3-benzoate, melting point 206°–207° C., 16% overall yield.

EXAMPLE XIV dl-17α-Ethynyl-11α-methyl-8α-oestra-1,3,5(10)-triene-3,17β-diol (formula (1): $R_1$=OH, $R_2$=H, $R_3$=methyl, $R_4$=(α-ethynyl)(βOH))

Acetylene was passed for 2 hours through a suspension of 1.7 g (15 mmol) potassium-t-butylate in 30 ml dry tetrahydrofuran which had been cooled to 0° C. The 17-ketone from example XIII (0.40 g, 1 mmol) dissolved in 20 ml dry tetrahydrofuran was added dropwise during stirring. Stirring was continued for 5 hours at 0°–5° C. whilst still passing acetylene through. The reaction mixture was mixed with water and extracted with ethyl acetate. The extracts were washed with water, dried on anhydrous magnesium sulphate and concentrated. The crude product was subjected to chromatography above 50 g silicagel with hexane/ethyl acetate 7:3 and recrystallised out of ethyl acetate/hexane. This gave 0.273 g 17α-ethynyl product (88% yield), melting point 186°–187° C.

EXAMPLE XV

11α-Methyl-8α-oestradiol methyl ether (formula (1): $R_1$=methoxy, $R_2$=H, $R_3$=methyl, $R_4$=H(βOH))

(a) The dl product from example III (1.5 g, 5 mmol) was dissolved in 10 ml pyridine. Phthalic acid anydride (3.0 g, 20 mmol) was added and the mixture was boiled under nitrogen for 2½ hours under reflux cooling. The reaction mixture was cooled, poured into 250 ml of 2 N hydrochloric acid and stirred for 3 hours at room temperature. The resultant deposit was sucked off, washed with warm water, dried and recrystallised out of dichloromethane/methanol. 2.5 g Hemiphthalate (96% yield) was obtained, melting point 225°–226° C.

(b) The hemiphthalate obtained in example XV(a) (2.15 g, 4.8 mmol) was suspended in 60 ml methanol, after which 1.41 g (4.8 mmol) cinchonine was added. The mixture was brought to the boil and then cooled slowly to 0° C. After standing for 4 hours at 0° C. the resultant deposit was sucked off (0.92 g). The filtrate was concentrated to a volume of 16 ml and, after adding an inoculation crystal, was stored for 16 hours at 0° C. The resultant deposit was sucked off (0.62 g). The filtrate was concentrated and once again was recrystalised in the same manner out of 10 ml methanol. From this 0.18 g of crystals were obtained, so that in total 1.72 g crystalline material was obtained.

(c) The crystalline cinchonine salt (1.72 g, 2.3 mmol) obtained in example XV(b) was suspended in 17 ml methanol and treated at 0° C. with 35 ml 3 N sulphuric acid. The mixture was stirred for 3 hours at 0° C. The resultant deposit was sucked off, washed with water until neutral, dried and recrystallised out of dichloromethane/methanol. 0.99 g d-hemiphthalate (95.5% yield) was obtained, melting point 225° C., $[\alpha]_D^{20}$= +42.3° (CHCl$_3$).

(d) The d-hemiphthalate (0.99 g, 2.2 mmol) obtained in example XV(d) was dissolved in 22 ml methanol. Potassium hydroxide (1.30 g, 23 mmol) was added and the mixture obtained was boiled for 5 hours under reflux cooling. The reaction mixture was cooled, mixed with water and extracted with dichloromethane. The extracts were washed until neutral with water, dried on anhydrous sodium sulphate and concentrated. The residue was recrystallised from 5 ml of ether. This gave 0.19 g crystals of optical impure compound, melting point 129°–133° C., $[\alpha]_D^{20}$= +9.5° (CHCl$_3$) and on evaporation of the mother-lye 0.41 g of optical pure 11α-methyl-8α-oestradiol methyl ether, melting point 122°–125° C., $[\alpha]_D^{20}$= +19.5° (CHCl$_3$) was obtained.

EXAMPLE XVI ent-11α-Methyl-8α-oestradiol methyl ether (formula (1): $R_1$=methoxy, $R_2$=H, $R_3$=methyl, $R_4$=H(βOH))

Evaporation of the mother liquor obtained in example XV(b) gave 1.86 g of low-melting point cinchonine salt. Decomposition with 3 N sulphuric acid as described in example XV(c) gave 0.94 g of l-hemiphthalate (84% yield), melting point 225° C., $[\alpha]_D^{20}$= −40.8° (CHCl$_3$).

Saponification of this, as described in example XV(d), supplied 0.49 g (76% yield) ent-11α-methyl-8α-oestradiol methyl ether, melting point 122°–126° C., $[\alpha]_D^{20}$= −17.7° (CHCl$_3$) and 0.18 g of optical less pure compound having a melting point of 129°–132° C. and $[\alpha]_D^{20}$ of −10.0° (CHCl$_3$).

EXAMPLE XVII

11α-Methyl-8α-oestradiol (formula (1): $R_1$=OH, $R_2$=H, $R_3$=methyl, $R_4$=H(βOH))

The methyl ether from example XV(d) was demethylated in a manner similar to that described in example VIII. The crude product was purified by chromatography above silicagel with hexane/acetone 8:2. The 11α-methyl-8α-oestradiol was isolated in quantitative yield, melting point 183°–185° C., $[\alpha]_D^{20} = +26.1°$ (tetrahydrofuran).

EXAMPLE XVIII ent-11α-Methyl-8α-oestradiol (formula (1): $R_1$=OH, $R_2$=H, $R_3$=methyl, $R_4$=H(βOH))

This enantiomer was obtained from the enantiomer from example XVI in a manner analogous to that described in examples VIII and XVII. Melting point 182°–184° C., $[\alpha]_D^{20} = -23.4°$ (tetrahydrofuran).

EXAMPLE XIX (a) 3-(3,5-dimethoxyphenyl)-propyltriphenyl phosphonium bromide (formula (2): $R_5 = R_6$=methoxy; A=P(phenyl)$_3$)

A mixture of 25.8 g (0.10 mol) 1-(3-bromopropyl)-3,5-dimethoxy benzene, 32.0 g (0.12 mol) triphenylphosphine and 50 ml toluene was heated for 16 hours at 110° C. The reaction mixture was cooled down and the resultant deposit was filtered off. The crystals were washed with toluene and dried. Yield 50.7 g of phosphonium bromide (97%), melting point 171°–172° C.

(b)
dl-(Z)-1-(3,5-dimethoxyphenyl)-5-methyl-7-(5-methyl-2-furyl)-3-heptene (formula (4): $R_3 = R_7 = CH_3$, $R_5 = R_6$=methoxy)

Wittig condensation of the phosphonium salt obtained in example XIX(a) with the aldehyde from example I(b) in the manner described in example I(c) gave, with 82% yield, the (Z)-isomer mentioned in the preamble mixed with approximately 10% (E) isomer.

(c)
dl-(Z)-2-[6-(3,5-dimethoxyphenyl)-2-methyl-3-hexenyl]-3-methyl-2-cyclopentenone (formula (6): $R_3 = R_7 = CH_3$, $R_5 = R_6$=methoxy)

The Wittig product from example XIX(b) was reacted in a manner analogous to that described in example I(d) to give the desired cyclopentenone. From the mixture originally obtained of 90% (Z)- and 10% (E)-isomer, the pure (Z) isomer was isolated with 72% yield.

(d)
dl-1,3-Dimethoxy-11α,17-dimethyl-8α-gona-1,3,5(10),13(17)-tetraene (formula (8): $R_1 = R_2$=methoxy, $R_3 = CH_3$)

The Z-isomer from example XIX(c) was reduced and cyclized in a manner analogous to that described in example I(e). The pure gonatetraene derivative was obtained by crystallisation from methanol with 64% yield, melting point 81°–82° C.

EXAMPLE XX dl-1-Methoxy-11α,17-dimethyl-8α-gona-1,3,5(10),13(17)-tetraene-3-ol (formula (8): $R_1$=OH, $R_2$=methoxy, $R_3 = CH_3$)

Treatment of the gonatetraene derivative from example XIX(c) with lithium diphenyl phosphide in a manner as described in example VIII gave the 1-methoxy-3-ol-derivative in 35% yield, melting point 150°–153° C.

EXAMPLE XXI dl-1,3-dimethoxy-11α-methyl-8α-oestra-1,3,5(10)-triene-17-one (formula (10): $R_1 = R_2$=methoxy, $R_3$=methyl)

The gonatetraene derivative from example XIX(c) was epoxidized as described in example II(a) and then treated with borotrifluoride etherate as described in example II(b). From this the desired 17-ketone was obtained with 17% yield.

EXAMPLE XXII dl-1,3-Dimethoxy-11α-methyl-8α-oestra-1,3,5(10)-triene-17β-ol (formula (1): $R_1 = R_2$=methoxy, $R_3$=methyl, $R_4$=H(βOH))

The 17-ketone from example XXI was reduced as described in example III to the oestradiol derivative, with 80% yield, melting point 91°–99° C.

EXAMPLE XXIII dl-11α-Methyl-8α-oestra-1,3,5(10)-triene-1,3,17-triol (formula (1): $R_1 = R_2$=OH, $R_3$=methyl, $R_4$=H(βOH))

The oestradiol derivative from example XXII (0.66 g, 2 mmol) was mixed with 35 ml dichloromethane and 0.66 ml boron tribromide and was heated for 30 minutes at 30° C. The reaction mixture was washed with sodium bicarbonate solution, dried on anhydrous $Na_2SO_4$ and concentrated. The residue was subjected to chromatography above silicagel with hexane/ethyl acetate 1:1 and the product was crystallised out of ether. Yield 0.43 g (80%) 1,3,17-triol, melting point 262°–264° C.

EXAMPLE XXIV dl-11α-Methyl-8α-oestra-1,3,5(10)-triene-1,3,17β-triol triacetate (formula (1): $R_1 = R_2$=acetoxy, $R_3$=methyl, $R_4$=H(β-acetoxy)).

The triol from example XXIII (0.1 g) was acetylated in pyridine (5 ml) with acetic acid anhydride (2 ml). After stirring for 1 hour at 75° C. the reaction mixture was diluted by carefully adding water. Processing in the normal manner gave, in fairly quantitative yield, dl-11α-methyl-8α-oestra-1,3,5(10)-triene-1,3,17β-triol triacetate.

I claim:
1. A compound selected from the group consisting of

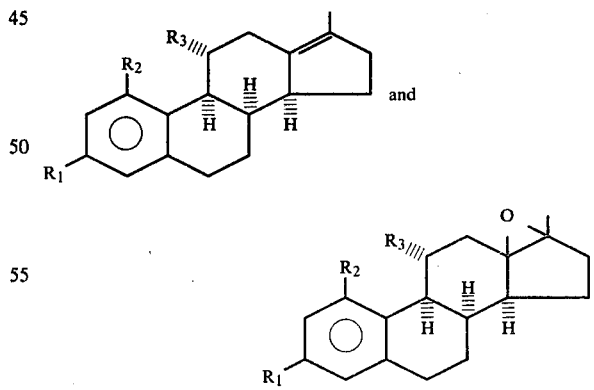

wherein
$R_1$=H, hydroxy, ($C_1$–$C_8$)-hydrocarbyloxy, trimethylsilyloxy, tetrahydropyranyloxy or ($C_1$–$C_7$)-carboxy-acyloxy;
$R_2$=H or equal to $R_1$; with the proviso that at least one of the substituents $R_1$ and $R_2$ is not equal to H; and
$R_3$=methyl or ethyl.

* * * * *